United States Patent
Yumioka

(10) Patent No.: US 10,695,276 B2
(45) Date of Patent: Jun. 30, 2020

(54) COMPOSITION CONTAINING GLYCEROL AND GLYCINE

(71) Applicant: AJINOMOTO CO., INC., Tokyo (JP)

(72) Inventor: Rina Yumioka, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 144 days.

(21) Appl. No.: 14/538,113

(22) Filed: Nov. 11, 2014

(65) Prior Publication Data

US 2015/0133567 A1 May 14, 2015

(30) Foreign Application Priority Data

Nov. 11, 2013 (JP) .................... 2013-233424

(51) Int. Cl.
| | | |
|---|---|---|
| *A61K 8/44* | (2006.01) | |
| *A61K 8/34* | (2006.01) | |
| *A61Q 19/00* | (2006.01) | |
| *A61Q 19/10* | (2006.01) | |

(52) U.S. Cl.
CPC ............... *A61K 8/44* (2013.01); *A61K 8/345* (2013.01); *A61K 8/442* (2013.01); *A61Q 19/00* (2013.01); *A61Q 19/10* (2013.01); *A61K 2800/262* (2013.01); *A61K 2800/30* (2013.01); *A61K 2800/42* (2013.01)

(58) Field of Classification Search
CPC .................... A61K 8/345; A61K 8/44
See application file for complete search history.

(56) References Cited

U.S. PATENT DOCUMENTS

| | | | |
|---|---|---|---|
| 5,603,923 | A | 2/1997 | Robinson et al. |
| 2005/0265951 | A1 | 12/2005 | Yamawaki et al. |
| 2008/0033191 | A1 | 2/2008 | Schoerken et al. |
| 2009/0093388 | A1 | 4/2009 | Yamawaki et al. |
| 2010/0314248 | A1 | 12/2010 | Worden et al. |
| 2012/0083039 | A1 | 4/2012 | Milek et al. |
| 2013/0029699 | A1 | 1/2013 | Hermanson et al. |
| 2013/0029899 | A1* | 1/2013 | Hermanson ............ A61K 8/345 510/535 |
| 2013/0030203 | A1* | 1/2013 | Harichian ............. C07C 231/02 554/69 |

FOREIGN PATENT DOCUMENTS

| | | |
|---|---|---|
| EP | 1 857 534 A1 | 11/2007 |
| EP | 1 864 647 A1 | 12/2007 |
| FR | 2 883 170 A1 | 9/2006 |
| JP | 7-173488 | 7/1995 |
| JP | 8-231335 A | 9/1996 |
| JP | 9-136810 A | 5/1997 |
| JP | 9-510971 A | 11/1997 |
| JP | 2000-143497 A | 5/2000 |
| JP | 2001-139448 A | 5/2001 |
| JP | 2002-179553 | 6/2002 |
| WO | 2004/020394 | 3/2004 |
| WO | WO 2004/105721 A1 | 12/2004 |
| WO | WO 2009/009391 A2 | 1/2009 |
| WO | WO 2012/068444 A2 | 5/2012 |

OTHER PUBLICATIONS

Demirel et al.; "Reaction kinetics and modelling of the gold catalysed glycerol oxidation"; 2007; Topics in Catalyxix; 44(1-2): 299-305.*
Kawashima et al.; "Nonenzymatic Browning Reactions of Dihydroxyacetone with Amino Acids or Their Esters"; 1980; Agric. Biol. Chem.; 44(7): 1595-1599.*
Lambers et al.; "Natural skin surface pH is on average below 5, which is beneficial for its resident flora"; 2006; International Journal of Cosmetic Science; 28: 359-370.*
Sarah Windsor, et al., "A convenient new analysis of dihydroxyacetone and methylglyoxal applied to Australian Leptospermum honeys", Journal of Pharmacognosy and Phytotherapy vol. 4(1), Jan. 2012 pp. 6-11, http://www.academicjournals.org/JPP.
French Preliminary Search Report and English translation of Written Opinion dated Feb. 27, 2015 in Patent Application No. 1460839 (with English translation of categories of cited documents).
*Handbook of Skin and Beauty Cosmetics Preparations*, Liu, Congmin et al., p. 135, Traditional Chinese Medicine Ancient Books Publishing House Dec. 31, 2004(with partial English translation).
Office Action dated Nov. 20, 2018 issued in corresponding Chinese patent application No. 201410632803.9 (English translation only).
Liu et al.—"Fine Chemical Production technology", published by Chemical Industry Press, Jun. 2000 (with partial English translation).
Jianfeiyufangshaiyao liangnierxing 2004, pp. 113-114.
http://www.120ask.com/question/24767481.htm EP 1864647 Pub: 2011.
Wittgenstein et al.-"Reaction of Dihydroxyacetone (DHA) With Human Skin Callus and Amino Compounds", The Journal of Investigative Dermatology, vol. 36, Apr. 1961, No. 4, pp. 283-286.
Saegusa, Senoo, analysis and test report—The Results of the analysis and examination requested on Nov. 9, 2017 with English translation dated Dec. 27, 2017, SCAS Sumika Chemical Analysis Service Chiba Laboratory (14 pages).
English translation of Office Action dated Mar. 15, 2018 issued in corresponding Japanese patent application 2013-233424.
English translation of Office Action dated Apr. 4, 2018 issued in corresponding Chinese patent application No. 201410632803.9.

* cited by examiner

*Primary Examiner* — Timothy P Thomas
(74) *Attorney, Agent, or Firm* — Oblon, McClelland, Maier & Neustadt, L.L.P.

(57) ABSTRACT

The present invention aims to provide a production method of a composition containing (A) glycerol and (B) glycine, which includes using glycerol substantially free of dihydroxyacetone or having a dihydroxyacetone content of not more than 150 ppm. According to the present invention, a composition, particularly a cosmetic composition, having a moist feeling but free of stickiness and showing suppressed coloration can be provided.

11 Claims, No Drawings

COMPOSITION CONTAINING GLYCEROL AND GLYCINE

TECHNICAL FIELD OF THE INVENTION

The present invention relates to a composition having a moist feeling, less stickiness, and suppressed coloration, particularly cosmetic composition. Particularly, it relates to a production method thereof and a method of suppressing coloration of the composition.

BACKGROUND OF THE INVENTION

When cosmetic agent and the like are prepared, glycerol is widely used to create a moist feeling. On the other hand, glycine is a material used as a cosmetic agent to moisturize the skin and simultaneously suppress stickiness, and N-acylglycine and a salt thereof are materials used for cosmetics as washing components.

Glycerol and glycine or N-acylglycine are often simultaneously added to cosmetics (patent documents 1, 2).

DOCUMENT LIST

Patent Documents patent document 1: JP-A-H07-173488
patent document 2: JP-A-2002-179553

SUMMARY OF THE INVENTION

Problems to be Solved by the Invention

The present inventors faced a problem of coloration when glycerol and glycine or N-acylglycine are blended. Therefore, the present invention aims to provide a composition containing glycerol and glycine or N-acylglycine and free of coloration, particularly, a cosmetic composition and a production method thereof. Moreover, it aims to provide a method of suppressing coloration when glycerol and glycine or N-acylglycine are added.

Means of Solving the Problems

The present inventors have conducted intensive studies in an attempt to solve the aforementioned problems and found that dihydroxyacetone contained in glycerol in a composition containing glycerol and glycine (or trace glycine contained in N-acylglycine) is involved in coloration, and that use of glycerol containing a less amount of dihydroxyacetone obviates the inconvenient phenomenon of coloration. They have conducted further studies and completed the present invention.

Accordingly, the present invention is as described below.
[1] A method of producing a composition comprising (A) glycerol and (B) glycine, comprising using glycerol substantially free of dihydroxyacetone or having a dihydroxyacetone content of not more than 150 ppm.
[2] The production method of [1], wherein the dihydroxyacetone content is not more than 100 ppm.
[3] The production method of [1], wherein the dihydroxyacetone content is not more than 40 ppm.
[4] The production method of any one of [1]-[3], wherein the concentration of (A) in the composition is 0.5-50 mass %.
[5] The production method of any one of [1]-[4], wherein the concentration of (B) in the composition is 0.01-5 mass %.
[6] The production method of any one of [1]-[5], wherein the mass ratio of (A):(B) is 5000:1-1:10.
[7] The production method of any one of [1]-[6], wherein the composition further contains at least one kind selected from (C) N-acylglycine and a salt thereof.
[8] A cosmetic composition comprising (A) glycerol substantially free of dihydroxyacetone or having a dihydroxyacetone content of not more than 150 ppm, and (B) glycine.
[9] The cosmetic composition of [8], which is a cleansing composition.
[10] A method of suppressing coloration of a composition comprising (A) glycerol and (B) glycine, comprising using glycerol substantially free of dihydroxyacetone or having a dihydroxyacetone content of not more than 150 ppm.
[11] Use of glycerol substantially free of dihydroxyacetone or having a dihydroxyacetone content of not more than 150 ppm for suppressing coloration of a composition comprising (A) glycerol and (B) glycine.

Effect of the Invention

According to the present invention, for example, a cosmetic composition for conditioning and protection of skin, which is free of coloration and superior in moisture sense of use, can be provided. According to the present invention, for example, a cleansing composition superior in the appearance, which affords cleaning without stickiness while maintaining a moist feeling, can be provided.

DETAILED DESCRIPTION OF THE PREFERRED EMBODIMENTS

The present invention relates to a method of producing a composition comprising (A) glycerol and (B) glycine, comprising using glycerol substantially free of dihydroxyacetone or having a dihydroxyacetone content of not more than 150 ppm (hereinafter to be also referred to as the production method of the present invention).

As (A) glycerol to be used in the production method of the present invention, glycerol substantially free of dihydroxyacetone or having a dihydroxyacetone content of not more than 150 ppm is used. The dihydroxyacetone content is preferably not more than 100 ppm, more preferably not more than 50 ppm, further preferably not more than 40 ppm, particularly preferably substantially none.

The term "substantially free of dihydroxyacetone" means that the glycerol contains not more than 20 ppm, which is the detection limit, preferably not more than 5 ppm, more preferably not more than 1 ppm, further preferably not more than 0.5 ppm, particularly preferably 0 ppm, of dihydroxyacetone.

The lower limit of the amount of dihydroxyacetone in the glycerol is preferably 5 ppm, more preferably 1 ppm, further preferably 0.5 ppm, particularly preferably 0 ppm.

Dihydroxyacetone in glycerol can be derivatized according to the PFBOA method and the amount thereof can be measured by LC-MS.

To make glycerol substantially free of dihydroxyacetone or set the amount thereof to not more than a desired content, a method of removing dihydroxyacetone from glycerol such as filtration, distillation, activated carbon treatment, ion exchange treatment, reduction reaction and the like can be mentioned.

When used as a cosmetic agent, the concentration of glycerol in the composition of the present invention is preferably not less than 0.5 mass %, more preferably not less than 1.0 mass %, further preferably not less than 5.0 mass %, to confer a moist feeling. In addition, to suppress stickiness, it is preferably not more than 50 mass %, more preferably not more than 40 mass %, and further preferably not more than 30 mass %.

As (B) glycine in the present invention, any of natural one derived from animal and plant and one obtained by chemical synthesis method, fermentation method or genetic recombination method may be used.

In addition, (B) glycine in the present specification encompasses trace glycine contained in N-acylglycine or a salt thereof. Glycine may be contained in N-acylglycine or a salt thereof since glycine used in the production process remains in a trace amount or N-acylglycine is sometimes decomposed to become glycine.

The concentration of glycine in the composition of the present invention when used as a cosmetic agent is preferably not less than 0.01 mass %, more preferably not less than 0.1 mass %, further preferably not less than 0.3 mass %, to suppress stickiness.

In addition, while the upper limit thereof is not particularly limited when the dihydroxyacetone content of glycerol is 0, it is preferably not more than 5 mass %, more preferably not more than 3 mass %, further preferably not more than 1 mass %, when dihydroxyacetone is contained. N-acylglycine or a salt thereof may contain glycine, and the above-mentioned glycine concentration also includes glycine contained in N-acylglycine or a salt thereof.

In the present invention, the mass ratio of (A):(B) is preferably 5000:1-1:10, more preferably 400:1-1:3, further preferably 100:1-5:1, to suppress coloration and stickiness.

In the present invention, the amount of glycine relative to dihydroxyacetone (glycine/dihydroxyacetone (mass/mass)) is preferably not less than 1.3, more preferably not less than 20, further preferably not less than 100, still more preferably not less than 1000, yet more preferably not less than 10000, still further preferably not less than 12000, from the aspect of coloration.

The composition in the present invention may further contain at least one kind selected from (C) N-acylglycine and a salt thereof.

As N-acylglycine or a salt thereof, any of those obtained by chemical synthesis method, fermentation method, and genetic recombination method may be used.

An acyl group of N-acylglycine or a salt thereof to be used in the present invention preferably has 8-22 carbon atoms. Examples thereof include an acyl group having a single composition such as an octanoyl group, a nonanoyl group, a decanoyl group, an undecanoyl group, a lauroyl group, a tridecanoyl group, a myristoyl group, a stearoyl group, a palmitoyl group, a behenoyl group, an isostearoyl group, an oleoyl group and the like; and a mixed fatty acid acyl group containing these such as a coconut oil fatty acid acyl group (also to be referred to as cocoyl group), a beef fat fatty acid acyl group, a hardened beef tallow fatty acid acyl group, a soybean oil fatty acid acyl group, a cotton seed oil fatty acid acyl group, a castor oil fatty acid acyl group, an olive oil fatty acid acyl group, a palm oil fatty acid acyl group, a palm kernel oil fatty acid acyl group and the like. Preferred are an octanoyl group, a decanoyl group, a lauroyl group, a myristoyl group, a palmitoyl group and a cocoyl group, more preferably a myristoyl group, a lauroyl group, a cocoyl group.

One or more kinds of N-acylglycine or a salt thereof having these acyl groups may be used in a mixture.

While the salt of N-acylglycine is not particularly limited, for example, alkali metal salts such as sodium salt, potassium salt and the like; alkaline earth metal salts such as magnesium salt, calcium salt and the like; alkanolamine salts such as triethanolamine salt and the like; ammonium salt; choline salt; and salt with basic amino acid such as lysine salt, ornithine salt, arginine salt and the like; can be mentioned. Preferred are alkali metal salt, alkanolamine salt and salt with basic amino acid, and sodium salt, potassium salt, triethanolamine salt and arginine salt are particularly preferable, from the aspects of easy availability, handleability and the like.

The concentration of N-acylglycine or a salt thereof in the composition of the present invention is not less than 1 mass %, preferably not less than 3 mass %, and more preferably not less than 5 mass %, to retain foaming property.

Moreover, the upper limit thereof is not more than 40 mass %, preferably not more than 30 mass %, and more preferably not more than 20 mass %.

In the present invention, the "cosmetic agent" generally aims to treat human body for the purpose of beautification, cleanliness, protection or deodorization, and includes skin care agents, hair care preparations, teeth and mouth care preparations and the like.

In the present invention, examples of the skin care agent include skin lotion for skin conditioning or protection, facial mask, skin milk, moisturizing cream, serum and the like, facial wash for cleansing (cream, paste, liquid, gel, aerosol, foam and the like), body shampoo, shower gel and the like.

Examples of the hair care preparation include shampoo for washing, hair treatment and the like.

Examples of the teeth and mouth care preparation include toothpaste for brushing of teeth, mouthwash for mouth freshener•cleansing and the like.

Of these, skin care agents and hair care preparations are preferable, and cleansing compositions for washing are preferable, to make use of the transparency of the dosage form and an emollient effect on the skin and hair.

The composition of the present invention can appropriately contain, besides the aforementioned essential components, various optional components to be used for general cosmetic agents, quasi-drugs and the like, at a level not inhibiting the effect of the present invention. For example, surfactant, oil solution, high molecular polymer, viscosity modifier, chelating agent, moisturizer, preservative, nutrition component, fine polymer powder, anti-inflammatory agent, antimicrobial agent, antioxidant, the other pearly sheen agent, UV absorber, pH adjuster, dye, flavor, physiologically active component and the like can be added as necessary within the range the effect of the present invention is not impaired.

Examples of the surfactant include anionic surfactant, nonionic surfactant, amphoteric surfactant, cationic surfactant, conditioning component and the like.

Examples of the anionic surfactant include fatty acid salt, polyoxyalkylene alkyl ether acetate, alkylsulfate, polyoxyalkylene alkyl ether sulfate, sulfosuccinate surfactant, alkylphosphate, polyoxyalkylene alkyl ether phosphate and the like. Examples of the nonionic surfactant include alkylpolyglucoside, sucrose fatty acid ester, polyglycerol fatty acid ester, polyoxyalkylene alkyl ether, fatty acid alkanolamide, alkylamine oxide, fatty acid polyvalent alcohol ester and the like. Examples of the cationic surfactant include straight chain or branched chain mono- or di-long chain alkyl quaternary ammonium salt, mono- or di-long chain alkyl tertiary amine and the like. Examples of the amphoteric surfactant include amide amino acid surfactant, carbobetaine surfactant, sulfobetaine surfactant, amidesulfobetaine surfactant, imidazolinium betaine surfactant, amino acid betaine surfactant, phosphobetaine surfactant and the like.

Examples of the conditioning component include oil solution such as higher alcohol, silicone, silicone derivative, lanolin, squalene, hydrocarbon, protein derivative, polyethylene glycol fatty acid ester and the like, cationized polymer such as cationic cellulose, cationized guar gum, Merquat 550 and the like and the like.

Examples of the oil solution include higher alcohol, silicone, silicone derivative, lanolin, squalene, hydrocarbon, protein derivative, fatty acid ester of polyethylene glycol, hydrogenated polyisobutene and the like. Examples of the high molecular polymer include methylcellulose, hydroxyethylcellulose, hydroxypropylmethylcellulose, carboxyvinyl polymer, acrylamide-acrylic acid-dimethyldiallylammonium chloride copolymer, xanthan gum and the like. Examples of the viscosity modifier include polyoxyalkylene sorbitan ester, polyoxyethylene glycol distearate, ethanol and the like; thickener such as hydroxypropylstarch phosphoric acid and the like. Examples of the chelating agent include ethylenediamine tetraacetic acid (EDTA), phosphonates and the like. Examples of the moisturizer include isopentyldiol, sorbitol and the like. Examples of the preservative include methylparaben, butylparaben and the like. Examples of the nutrition substance include vitamin (acetic acid d-α-tocopherol etc.) or a derivative thereof, precursor and the like, animal and plant extracts such as lecithin, gelatin and the like or a derivative thereof. Examples of the fine polymer powder include nylon, polyethylene and the like. Examples of the anti-inflammatory agent include potassium glycyrrhizinate and the like. Examples of the antimicrobial agent include triclosan, triclocarban, octopirox, zinc pyrithione and the like. Examples of the antioxidant include dibutylhydroxytoluene and the like, soap component such as potassium myristate and the like.

The pH of the composition of the present invention as a cosmetic agent can be used after adjusting to a wide range of pH 3-pH 10. The range of pH 4-pH 8 is more preferable, and pH 5-pH 8 is further preferable, since stimulation to the skin, eye, hair and the like can be reduced, and viscosity suitable for liposolubility and superior foam texture can be obtained.

The composition of the present invention can contain an amino acid other than glycine. Examples thereof include arginine, aspartic acid, alanine, serine, valine, proline, threonine, histidine, phenylalanine, arginine and the like, which can be added according to specific use and dosage form.

The composition of the present invention can be applied to all animals such as human, animal other than human [for example, mammals other than human (domestic animals and pet animals such as swine, bovine, horse, dog and the like, birds (poultries and pet animals such as turkey, chicken and the like) and the like] and the like.

The production method of the composition of the present invention is not particularly limited except that glycerol having a dihydroxyacetone content of not more than 150 ppm is used, and known steps may be combined as appropriate.

In addition, a composition, particularly a cosmetic composition, produced by the method of the present invention and showing suppressed coloration is also encompassed in the present invention.

Specific examples thereof include a cosmetic composition comprising (A) glycerol substantially free of dihydroxyacetone or having a dihydroxyacetone content of not more than 150 ppm, and (B) glycine.

The cosmetic composition may also be a cleansing composition.

The transmittance of the composition produced by the method of the present invention and showing suppressed coloration is a value measured by a spectrophotometer at a wavelength of 430 nm using a 1 centimeter quartz cell. When the total concentration of (A) glycerol and (B) glycine is 35%, it is preferably not less than 85%, more preferably not less than 90%, further preferably not less than 93%, particularly preferably not less than 94%.

The present invention further provides a method of suppressing coloration of a composition comprising (A) glycerol and (B) glycine, comprising using glycerol substantially free of dihydroxyacetone or having a dihydroxyacetone content of not more than 150 ppm.

The definitions of (A) glycerol and (B) glycine, and the like are as mentioned above.

EXAMPLES

While the present invention is explained in more detail in the following by referring to Examples, the scope of the Examples of the present invention is not limited thereby. In the present specification, "ppm" means "mass ppm" unless otherwise specified.

<Purification of Glycerol>

As glycerol of Table 1, glycerol manufactured by Lion Corporation (dihydroxyacetone amount in glycerol, 200 ppm) was directly used.

On the other hand, glycerol in Tables 2-5 was obtained by repeatedly distilling glycerol manufactured by Lion Corporation at 10-20 mbar under reduced pressure at 165-180° C. until dihydroxyacetone in glycerol became undetectable, treating same with activated carbon, and adjusting same to a desired dihydroxyacetone amount by adding dihydroxyacetone (manufactured by MP Biomedical).

<Analysis of Dihydroxyacetone>

As for the amount of dihydroxyacetone in glycerol, dihydroxyacetone was derivatized with aqueous pentafluorobenzylhydroxylamine (PFBOA) hydrochloride solution based on Journal of Pharmacognosy and Phytotherapy Vol. 4(1), pp. 6-11, January 2012, and detected and measured by LC-MS.

system: LCMS-2010A (LCMS solution data system manufactured by SHIMADZU CORPORATION)
column: SynergiFusion column (75×4.6 mM, 4 μm, particle size)
detection: MS
injection volume: 10 μm
column temperature: 45° C.
mobile phase A: acetonitrile
mobile phase B: water <Glycine, Acylglycine>

Glycine manufactured by Ajinomoto Co., Inc. was directly used. As acylglycine, cocoylglycine potassium salt (cocoylglycine K), GCK-12K, manufactured by Ajinomoto Co., Inc. was directly used.

<Analysis of Glycine>

As for the amount of glycine in N-acylglycine, glycine was labeled by using AccQ Tag (manufactured by Waters) fluorescence derivatizing reagent and measured.
system: UPLC TUV system (Empower 2 software manufactured by Waters)
column: ACQUITYA UPLC BHE C18, 1.7 μm, 2.1×150 mm
detection: UV (260 nm)
injection volume: 1 μm
column temperature: 45° C.
mobile phase A: AccQ-Tag Ultraeluent A 50 mL+ion exchange water 950 mL mobile phase B: AccQ-Tag Ultraeluent B
flow rate: 0.5 mL/min <Coloration Evaluation Method and Evaluation Criteria>

The coloration property of a composition was confirmed by mixing each composition described in Tables 1-5 by heating at 80° C. for 1 hr and, after cooling, measuring the transmittance at 430 nm by a spectrophotometer. The coloration property was judged according to the following evaluation criteria depending on the transmittance.

⊙: not less than 94%, ○: not less than 90%-less than 94%, Δ: not less than 87%-less than 90%, x: less than 87%.

In the Tables, dihydroxyacetone is shown by ppm in glycerol.

Other components are shown by mass % relative to the mass of the composition as a whole as 100.

In the Tables, the amount of glycine is the total of glycine in N-acylglycine and glycine added.

<Test Method and Evaluation Criteria of Moist Feeling>

Each composition (1.0 g) was foamed, showered away with tap water at 35-40° C. for 1 min, and water was wiped with a towel. The skin after drying was evaluated by 5 panelists.

The evaluation criteria were as follows.
4: moist feeling was strongly felt
3: moist feeling was somewhat felt,
2: normal,
1: moist feeling was not felt much,
0: moist feeling was not felt.

Average of not less than 3.0 ⊙, not less than 2.0 and less than 3.0 ○, not less than 1.0 and less than 2.0 Δ, less than 1.0 x.

<Test Method and Evaluation Criteria of Stickiness>

Each composition (1.0 g) described in Tables 2-5 was foamed, showered away with tap water at 35-40° C. for 1 min, and water was wiped with a towel. The skin after drying was evaluated by 5 panelists.

The evaluation criteria were as follows.
4: completely no stickiness
3: no stickiness,
2: normal,
1: somewhat sticky,
0: sticky.

Average of not less than 3.0 ⊙, not less than 2.0 and less than 3.0 ○, not less than 1.0 and less than 2.0 Δ, less than 1.0 x.

TABLE 1

|  | Example 1-1 | Comparative Example 1-1 |
|---|---|---|
| glycerol (after distillation) | 30.0 |  |
| glycerol (commercially available product as is) |  | 30.0 |
| cocoylglycine K | 18.0 | 18.0 |
| glycine | 0.56 | 0.56 |
| water | to 100 | to 100 |
| transmittance (430 nm) | 96.7 | 82.3 |
| coloration | ⊙ | X |

As shown in Table 1, Comparative Example 1-1 using glycerol with the amount of dihydroxyacetone in glycerol of 200 ppm showed coloration. On the other hand, Example 1-1 using glycerol free of dihydroxyacetone showed no coloration.

To examine the relationship between the amount of dihydroxyacetone in glycerol and coloration, the results of Table 2 were obtained by using glycerol with adjusted amount of dihydroxyacetone. In addition, a moist feeling and stickiness of the composition as a whole were also evaluated.

TABLE 2

|  | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 |
|---|---|---|---|---|---|---|---|---|---|---|
| glycerol | 30.0 | 30.0 | 30.0 | 30.0 | 30.0 | 30.0 | 30.0 | 30.0 | 30.0 | 30.0 |
| dihydroxyacetone (in glycerol: ppm) | 0 | 33 | 67 | 100 | 133 | 150 | 167 | 333 | 500 | 667 |
| cocoylglycine K | 18.0 | 18.0 | 18.0 | 18.0 | 18.0 | 18.0 | 18.0 | 18.0 | 18.0 | 18.0 |
| glycine | 0.06 | 0.06 | 0.06 | 0.06 | 0.06 | 0.06 | 0.06 | 0.06 | 0.06 | 0.06 |
| water | to 100 | to 100 | to 100 | to 100 | to 100 | to 100 | to 100 | to 100 | to 100 | to 100 |
| transmitttance (430 nm) | 97 | 95.9 | 95.4 | 94.7 | 94.3 | 95.9 | 89.8 | 87.1 | 80.1 | 73.3 |
| coloration | ⊙ | ⊙ | ⊙ | ⊙ | ⊙ | ⊙ | Δ | Δ | X | X |
| moist feeling | ⊙ | ⊙ | ⊙ | ⊙ | ⊙ | ⊙ | ⊙ | ⊙ | ⊙ | ⊙ |
| stickiness | ○ | ○ | ○ | ○ | ○ | ○ | ○ | ○ | ○ | ○ |

As shown in Table 2, when glycerol with dihydroxyacetone at 150 ppm or below was used, coloration was suppressed, and a composition with a moist feeling but free of stickiness was obtained.

TABLE 3

|  | Ex. 7 | Ex. 8 | Ex. 9 | Ex. 10 | Ex. 11 | Ex. 12 | Comp. Ex. 5 | Comp. Ex. 6 |
|---|---|---|---|---|---|---|---|---|
| glycerol | 30.0 | 30.0 | 30.0 | 30.0 | 30.0 | 30.0 | 30.0 | 30.0 |
| dihydroxyacetone (in glycerol: ppm) | 0 | 33 | 67 | 100 | 133 | 150 | 167 | 200 |

TABLE 3-continued

|  | Ex. 7 | Ex. 8 | Ex. 9 | Ex. 10 | Ex. 11 | Ex. 12 | Comp. Ex. 5 | Comp. Ex. 6 |
|---|---|---|---|---|---|---|---|---|
| cocoyl-glycine K | 18.0 | 18.0 | 18.0 | 18.0 | 18.0 | 18.0 | 18.0 | 18.0 |
| glycine | 0.56 | 0.56 | 0.56 | 0.56 | 0.56 | 0.56 | 0.56 | 0.56 |
| water | to 100 | to 100 | to 100 | to 100 | to 100 | to 100 | to 100 | to 100 |
| transmittance (430 nm) | 96.7 | 94.1 | 92.8 | 92.4 | 90.6 | 90.4 | 87.1 | 82.3 |
| coloration | ⊙ | ⊙ | ○ | ○ | ○ | ○ | Δ | X |
| moist feeling | ⊙ | ⊙ | ⊙ | ⊙ | ⊙ | ⊙ | ⊙ | ⊙ |
| stickiness | ⊙ | ⊙ | ⊙ | ⊙ | ⊙ | ⊙ | ⊙ | ⊙ |

As shown in Table 3, when glycine was increased and glycerol with dihydroxyacetone at 150 ppm or below was used, a composition with suppressed coloration and a moist feeling but free of stickiness was obtained

TABLE 4

|  | Ex. 1 | Ex. 13 | Ex. 14 | Ex. 7 | Ex. 15 | Ex. 16 |
|---|---|---|---|---|---|---|
| glycerol | 30.0 | 30.0 | 30.0 | 30.0 | 30.0 | 30.0 |
| dihydroxyacetone (in glycerol: ppm) | 0 | 0 | 0 | 0 | 0 | 0 |
| cocoyl-glycine K | 18.0 | 18.0 | 18.0 | 18.0 | 18.0 | 18.0 |
| glycine | 0.06 | 0.16 | 0.26 | 0.56 | 1.06 | 2.06 |
| water | to 100 | to 100 | to 100 | to 100 | to 100 | to 100 |
| transmittance (430 nm) | 97 | 95.6 | 96 | 96.7 | 97.2 | 96.6 |
| coloration | ⊙ | ⊙ | ⊙ | ⊙ | ⊙ | ⊙ |
| moist feeling | ⊙ | ⊙ | ⊙ | ⊙ | ⊙ | ⊙ |
| stickiness | ○ | ⊙ | ⊙ | ⊙ | ⊙ | ⊙ |

As shown in Table 4, when glycerol free of dihydroxyacetone was used, a composition without coloration and having a moist feeling bur free of stickiness was obtained even when glycine content was high.

TABLE 5

|  | Ex. 2 | Ex. 17 | Ex. 18 | Ex. 8 | Ex. 19 | Ex. 20 |
|---|---|---|---|---|---|---|
| glycerol | 30.0 | 30.0 | 30.0 | 30.0 | 30.0 | 30.0 |
| dihydroxyacetone (in glycerol: ppm) | 33 | 33 | 33 | 33 | 33 | 33 |
| cocoyl-glycine K | 18.0 | 18.0 | 18.0 | 18.0 | 18.0 | 18.0 |
| glycine | 0.06 | 0.16 | 0.26 | 0.56 | 1.06 | 2.06 |
| water | to 100 | to 100 | to 100 | to 100 | to 100 | to 100 |
| transmittance | 95.9 | 94.9 | 95.8 | 94.1 | 94.4 | 94.9 |
| coloration | ⊙ | ⊙ | ⊙ | ⊙ | ⊙ | ⊙ |
| moist feeling | ⊙ | ⊙ | ⊙ | ⊙ | ⊙ | ⊙ |
| stickiness | ○ | ⊙ | ⊙ | ⊙ | ⊙ | ⊙ |

As shown in Table 5, when glycerol with a small amount of dihydroxyacetone was used, a composition having a moist feeling but free of stickiness and showing suppressed coloration was obtained.

Formulation Example 1

Foamy Facial Wash

| component | (mass %) |
|---|---|
| cocoylglycine Na | 3.00 |
| glycine | 0.30 |
| glycerol | 10.00 |
| hydrogenated polyisobutene | 1.10 |
| PEG-20 glyceryl triisostearate | 2.70 |
| isopentyldiol | 10.00 |
| lauramidopropyl hydroxysultaine | 4.20 |
| lauryl glucoside | 1.00 |
| Lauroyl arginine | 0.02 |
| EDTA-2 Na | 0.10 |
| preservative | appropriate |
| flavor | appropriate |
| water | balance |
|  | 100.00 |

Formulation Example 2

Foaming Facial Cleanser

| component | (mass %) |
|---|---|
| cocoylglycine K | 32.00 |
| glycine | 0.10 |
| glycerol | 17.00 |
| potassium myristate | 1.50 |
| behenyl alcohol | 0.50 |
| citric acid | 2.60 |
| butylene glycol (BG) | 15.00 |
| glycol distearate | 2.50 |
| polyquaternium-7 | 0.04 |
| water | balance |
|  | 100.00 |

Formulation Example 3

Foaming Facial Cleanser

| component | (mass %) |
|---|---|
| cocoylglycine K | 11.13 |
| glycine | 1.00 |
| glycerol | 7.00 |
| sodium lauroamphoacetate | 4.98 |

-continued

| component | (mass %) |
|---|---|
| lauramidopropyl betaine | 4.30 |
| acrylates copolymer | 1.50 |
| petrolatum | 12.00 |
| lauric acid | 5.00 |
| hydroxypropyl starch phosphoric acid | 5.00 |
| preservative | q.s. |
| water | balance |
| | 100.00 |

Formulation Example 4

Foaming Facial Cleanser

| component | (mass %) |
|---|---|
| cocoylglycine Na | 16.50 |
| glycine | 1.50 |
| glycerol | 28.00 |
| sodium lauroamphoacetate | 2.40 |
| polyquaternium-39 | 0.10 |
| EDTA-2Na | 0.05 |
| citric acid | 1.20 |
| hydroxypropylmethylcellulose | 0.04 |
| preservative | q.s. |
| water | balance |
| | 100.00 |

Formulation Example 5

Body Shampoo

| component | (mass %) |
|---|---|
| cocoylglycine K | 4.5 |
| glycine | 0.5 |
| glycerol | 3.0 |
| potassium laurate | 11.0 |
| potassium myristate | 6.0 |
| sorbitol | 1.4 |
| glycol distearate | 2.0 |
| hydroxyethylcellulose | 0.5 |
| preservative | q.s. |
| flavor | q.s. |
| water | balance |
| | 100.0 |

Formulation Example 6

Body Shampoo

| component | (mass %) |
|---|---|
| cocoylglycine K | 1.00 |
| glycine | 0.30 |
| glycerol | 1.00 |
| sodium laureth sulfate | 5.04 |
| NaCl | 1.00 |

-continued

| component | (mass %) |
|---|---|
| sodium cocoyl isethionate | 3.30 |
| hydroxypropyl starch phosphoric acid | 5.00 |
| petrolatum | 5.00 |
| cocamidopropyl betaine | 5.10 |
| citric acid | q.s. |
| flavor | q.s. |
| water | q.s. |
| | 100.00 |

Formulation Example 7

Skin Lotion

| component | (mass %) |
|---|---|
| glycine | 0.20 |
| glycerol | 3.00 |
| butyleneglycol | 1.00 |
| dipropyleneglycol | 6.00 |
| sodium pyrrolidonecarboxylate | 0.10 |
| PEG-40 hydrogenated castor oil | 0.05 |
| citric acid | 0.03 |
| sodium hydroxide | q.s. |
| carboxyvinyl polymer | 0.07 |
| preservative | q.s. |
| water | balance |
| | 100.00 |

Formulation Example 8

Skin Cream

| component | (mass %) |
|---|---|
| glycine | 0.8 |
| glycerol | 6.0 |
| decamethylcyclopentasiloxane | 8.0 |
| octyl isopelargrate | 5.0 |
| cetyl 2-ethylhexanoate | 3.0 |
| glyceryl diisostearate | 1.3 |
| dimethicone copolyol | 6.5 |
| acetic acid-d-α-tocopherol | 0.1 |
| anhydrous magnesium sulfate | 1.5 |
| 1,3-butyleneglycol | 1.8 |
| preservative | q.s. |
| water | balance |
| | 100.0 |

Formulation Example 9

Conditioner

| component | (mass %) |
|---|---|
| glycine | 0.03 |
| glycerol | 2.00 |
| sodium pyrrolidonecarboxylate | 0.30 |

-continued

| component | (mass %) |
|---|---|
| sodium lactate | 0.24 |
| arginine | 0.16 |
| aspartic acid | 0.10 |
| pyrrolidone carboxylate | 0.09 |
| alanine | 0.02 |
| serine | 0.02 |
| valine | 0.01 |
| proline | 0.01 |
| threonine | 0.01 |
| isoleucine | 0.01 |
| histidine | 0.0032 |
| phenylalanine | 0.0032 |
| cetrimonium chloride | 8.30 |
| steareth-20 | 0.50 |
| cetanol | 6.00 |
| jojoba seed oil | 1.00 |
| preservative | appropriate |
| flavor | q.s. |
| water | balance |
| | 100.00 |

In all Formulation Examples, purified glycerol was used, and dihydroxyacetone as impurity was not more than the detection limit (20 ppm).

This application is based on a patent application No. 2013-233424 filed in Japan, the contents of which are incorporated in full herein.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of producing a composition, comprising:
   (A) glycerol;
   (B) glycine; and
   (C) at least one member selected from the group consisting of an N-acylglycine and a salt thereof,
   said method comprising combining glycine and the N-acylglycine or salt thereof with glycerol that has a dihydroxyacetone content of not more than 40 ppm by mass, to obtain a composition comprising (A) 0.5 to 30 mass % of the glycerol, (B) 0.01 to 1 mass % of the glycine, and (C) 3 to 30 mass % of the N-acylglycine or salt thereof, wherein the composition has a pH of 4 to 8.

2. The method according to claim 1, wherein the mass ratio of (A):(B) is 100:1 to 5:1.

3. The method according to claim 1, wherein the composition comprises (A) 1.0 to 30 mass % of the glycerol.

4. The method according to claim 1, wherein the composition comprises (A) 5.0 to 30 mass % of the glycerol.

5. The method according to claim 1, wherein the composition comprises (B) 0.1 to 1 mass % of the glycine.

6. The method according to claim 1, wherein the composition comprises (B) 0.3 to 1 mass % of the glycine.

7. The method according to claim 1, wherein the N-acylglycine or salt thereof has an acyl group comprising 8 to 22 carbon atoms.

8. The method according to claim 7, wherein the acyl group is selected from the group consisting of an octanoyl group, a decanoyl group, a lauroyl group, a myristoyl group, a palmitoyl group and a cocoyl group.

9. The method according to claim 7, wherein the acyl group is a cocoyl group.

10. The method according to claim 1, wherein the composition comprises (C) 5 to 20 mass % of the N-acylglycine or salt thereof.

11. The method according to claim 1, wherein the mass ratio of the glycine to the dihydroxyacetone is not less than 20.

* * * * *